(12) United States Patent
Broekaert et al.

(10) Patent No.: US 7,291,458 B2
(45) Date of Patent: Nov. 6, 2007

(54) LEPTIN-MEDIATED GENE-INDUCTION

(75) Inventors: Daniel Broekaert, Waarschool (BE); Joël S. Vandekerckhove, Loppem (BE); Annick Verhee, Lichtervelde (BE); Wim Waelput, Nieuwerkerken-Waas (BE); Jan Tavernier, Balegem (BE)

(73) Assignee: Vlaams Interuniversitair Instituut Voor Biotechnologie VZW, Zwijnaarde (BE)

( * ) Notice: Subject to any disclaimer, the term of this patent is extended or adjusted under 35 U.S.C. 154(b) by 509 days.

(21) Appl. No.: 10/235,264

(22) Filed: Sep. 4, 2002

(65) Prior Publication Data

US 2003/0036526 A1 Feb. 20, 2003

Related U.S. Application Data

(63) Continuation of application No. 09/770,735, filed on Jan. 26, 2001, now abandoned, which is a continuation of application No. PCT/EP99/05489, filed on Jul. 27, 1999.

(30) Foreign Application Priority Data

Jul. 28, 1998 (EP) ................... 98202524

(51) Int. Cl.
*C12Q 1/68* (2006.01)
(52) U.S. Cl. .................. 435/6; 435/69.1; 435/353; 530/351
(58) Field of Classification Search ............... 425/85.1; 435/7.95, 6
See application file for complete search history.

(56) References Cited

U.S. PATENT DOCUMENTS

| | | | |
|---|---|---|---|
| 5,521,066 A | 5/1996 | Menzel et al. |
| 5,686,281 A | 11/1997 | Roberts |
| 5,716,622 A | 2/1998 | Darnell et al. |
| 5,744,314 A | 4/1998 | Menzel et al. |
| 5,776,689 A | 7/1998 | Karin et al. |
| 5,843,697 A | 12/1998 | Pestka et al. |
| 5,885,779 A | 3/1999 | Sadowski et al. |
| 5,972,621 A | 10/1999 | Tartaglia et al. |
| 6,001,816 A | 12/1999 | Morsy et al. |
| 6,270,964 B1 | 8/2001 | Michnick et al. |
| 6,294,330 B1 | 9/2001 | Michnick et al. |
| 6,303,319 B1 | 10/2001 | Rickles |
| 6,342,345 B1 | 1/2002 | Blau et al. |
| 6,734,006 B2 | 5/2004 | Xiao et al. |
| 2001/0023062 A1 | 9/2001 | Ostade et al. |

FOREIGN PATENT DOCUMENTS

| EP | 0 646 644 A2 | 4/1995 |
|---|---|---|
| EP | 0832219 | 1/1997 |
| EP | 0912609 | 12/1997 |
| WO | WO 97/00319 | 1/1997 |
| WO | WO 97/20933 | 6/1997 |
| WO | WO 97/26335 | 7/1997 |
| WO | WO 97/31113 | 8/1997 |
| WO | WO 98/02542 | 1/1998 |
| WO | WO 98/12224 | 3/1998 |
| WO | WO 98/20158 | 5/1998 |
| WO | WO 98/34120 | 8/1998 |
| WO | WO 98/44350 | 10/1998 |
| WO | WO 99/03974 | 1/1999 |
| WO | WO 99/40946 A2 | 8/1999 |
| WO | WO 00/06722 | 2/2000 |
| WO | WO 00/07014 | 2/2000 |
| WO | WO 00/07038 | 2/2000 |
| WO | WO 02/40543 A1 | 5/2002 |
| WO | WO 02/062833 A2 | 8/2002 |

OTHER PUBLICATIONS

Baumann et al., Proc. Natl. Acad. Sci. USA 93: 8374-8378, 1996.*
David et al., J. Biol. Chem. 271: 4585-4588, 1996.*
Ghilardi et al., Proc. Natl. Acad. Sci. USA 93: 6231-6235, 1996.*
Nakashima et al., FEBS, 403: 79/82, 1997.*
Bjorbaek et al., Mol. Cell. 1: 619-625, 1998.*
Ray et al., J. Clin. Invest. 97: 1852-1859, 1996.*
Iyengar, R, FASEB J. 7: 768-775, 1993.*
Beattie et al., "Obesity and Hyperleptinemia in Metallothionein (-I and -II) Null Mice", Proceedings of the National Academy of Sciences of USA, vol. 95, Jan. 1998, pp. 358-363.
Bjorback et al., "Identification of SOCS-3 as a Potential Mediator of Central Leptin Resistance", Molecular Cell, vol. 1, No. 4, Mar. 1998, pp. 619-625.
Vaisse et al., "Leptin Activation of Stat3 in the Hypothalamus of Wild-Type and ob/ob Mice but not db/db Mice", Nature Genetics, vol. 14, Sep. 14, 1996, pp. 95-97.

(Continued)

*Primary Examiner*—Robert S. Landsman
*Assistant Examiner*—Gyan Chandra
(74) *Attorney, Agent, or Firm*—TraskBritt

(57) ABSTRACT

Methods of activating a signaling cascade comprising, introducing leptin and/or a cytokine to a receptor complex comprising gp 130, optionally in combination with a compound acting on adenylate cyclase or acting on one or more downstream targets of adenylate cyclase, thereby inducing genes in neuro-endocrine cells or cells of neuro-endocrine origin. Two distinct gene-sets are induced, immediate early response genes (STAT-3, SOCS-3, Metallothionein-II, the serine/threonine kinase Fnk and the rat homologue of MRF-1), and late induced target genes (Pancreatitis Associated Protein I, Squalene Epoxidase, Uridinediphosphate Glucuronyl Transferase and Annexin VIII). Strong co-stimulation with the adenylate cyclase activator forskolin was shown with respect to late induced target genes. Transcripts encoding Leptin Induced Protein I (LIP-I) and Leptin Induced Protein II (LIP-II) were identified; however, no forskolin co-stimulatory effect was observed. It is also demonstrated that leptin modulates in vivo expression of MT-II, Fnk and Pancreatitis Associated Protein I genes.

20 Claims, 10 Drawing Sheets

OTHER PUBLICATIONS

Waelput et al., "Analysis of Signal Transduction via the Leptin Receptor", International Journal of Obesity, vol. 22, No. Suppl. 3, Aug. 1998, p. S99.

PCT International Preliminary Examination Report, PCT/EP99/05489, dated Oct. 5, 2000.

PCT International Search Report, PCT/EP99/05489, dated Feb. 2, 2000, 6 pages.

PCT Written Opinion, PCT/EP99/05489, dated May 19, 2000, 8 pages.

Reply to Written Opinion for PCT/EP99/05489, letter dated Aug. 17, 2000, 6 pages.

Dusetti et al. Structural organization of the gene encoding the rat pancreatitis-associated protein vol. 268, Jul. 5, 1993, pp. 14470-14475.

Dusetti et al. The pancreatitis-associated protein I promoter allows targeting to the pancreas of a foreign gene whose expression is un-regulated during pancreatic inflammation pp. 5800-5804, Feb. 28, 1997.

Daly et al., Recognition of human colon cancer by T cells transduced with a chimeric receptor gene, Cancer Gene Therapy, 2000, pp. 284-291, vol. 7, No. 2.

Eyckerman et al., Design and application of a cytokine-receptor-based interaction trap, Nature Cell Biology, Dec. 2001, pp. 1114-1119, vol. 3, EBSCO Publishing.

Stoffel et al., Permissive role of thrombopoietin and granulocyte colony-stimulating factor receptors in hematopoietic cell fate decision in vivo, Proc. Natl. Acad. Sci., Jan. 1999, pp. 698-702, vol. 96.

Bjorbaek et al., The Role of SOCS-3 in Liptin Signaling and Leptin Resistance, The Journal of Biological Chemistry, Oct. 15, 1999, pp. 30059-30065, vol. 274, No. 42.

Bonnefoy-Berard et al., Vav: Function and Regulation in Hematopoietic Cell Signaling, Stem Cells, 1996, pp. 250-268, vol. 14.

Gisselbrecht, The CIS/SOCS proteins: a family of cytokine-inducible regulators of signaling, European Cytokine Network, Dec. 1999, pp. 463-470, vol. 10, No. 4.

Lee et al., Abnormal splicing of the leptin receptor in diabetic mice, Nature, Feb. 15, 1996, pp. 632-635, vol. 379.

Mercer et al., Localization of leptin receptor mRNA and the long form splice variant (OB-Rb) in mouse hypothalamus and adjacent brain regions by in situ hybridization, FEBS Letters, 1996, pp. 113-116, vol. 387.

Tartaglia et al., Identification and Expression Cloning of a Leptin Receptor, OB-R, Cell, Dec. 29, 1995, pp. 1263-1271, vol. 83.

Zabeau et al., The ins and outs of leptin receptor activation, FEBS Letters, 2003, pp. 45-50, vol. 546.

Banks et al., Activation of Downstream Signals by the Long Form of the Leptin Receptor, Journal of Biological Chemistry, May 12, 2000, pp. 14563-14572, vol. 275, No. 19, U.S.A.

Campfield et al., Science, 1998, pp. 1383-1389, vol. 280.

Carpenter et al., Proc. Natl. Acad. Sci. USA, 1998, pp. 6061-6066, vol. 95.

Colas et al., The impact of two-hybrid and related methods on biotechnology, Trends in Biotechnology, Aug. 1998, pp. 355-363, vol. 16.

Eyckerman et al., Analysis of Tyr to Phe and fa/fa leptin receptor mutations in the PC12 cell line, Eur. Cytokine Netw, Dec. 1999, pp. 549-556, vol. 10, No. 4.

Fields et al., The two-hybrid system: an assay for protein-protein interactions, Trends in Genetics, Aug. 1994, pp. 286-292, vol. 10, No. 8.

Grasso et al., Endocrinol, 1997, pp. 1413-1418, vol. 138.

Ihle et al., Jaks and Stats in signaling by the cytokine receptor superfamily, Trends Genet., Feb. 1995, pp. 69-74, vol. 11, No. 2.

Medici et al., The EMBO Journal 1997, pp. 7241-7249, vol. 16, No. 24.

Montoye et al., Analysis of leptin signalling in hematopoietic cells using an adapted MAPPIT strategy, FEBS Letters, 2006, pp. 3301-3307, vol. 580.

Montoye et al., In Press, A systematic scan of interactions with tyrosine motifs in the erythropoietin receptor using a mammalian two-hybrid approach.

Ngo et al., The Protein Folding Problem and Tertiary Structure Prediction, Chapter 14: Computational Complexity Protein Structure Prediction, and the Levinthal Paradox, Mar. 2, 1994, pp. 492-495.

Okuda et al., Ann N Y Acad Sci, 1999, pp. 305-312, vol. 872.

Osborne et al., The Yeast Tribrid System—Genetic Detection of trans-phosphorylated ITAM-SH2-Interactions, Biotechnology, Dec. 13, 1995, pp. 1474-1478, vol. 13.

Overton et al., Current Biology, 2000, pp. 341-344, vol. 10, No. 6.

Rohner-Jearnrenaud et al., The New Eng. J. Med. 1996, pp. 324-325, vol. 334.

Saitoh et al., Identification of Important Regions in the Cytoplasmic Justamembrane Domain of Type I Receptor That Separate Signaling Pathways of Transforming Growth Factor-beta, The Journal of Biological.

Shores et al., Curr Opin Immunol 1997, pp. 380-389, vol. 9, No. 3.

Verploegen et al., FEBS Letters, 1997 pp. 237-240, vol. 405.

Wells, Additivity of Mutational Effects in Proteins, Biochemistry, Sep. 18, 1990, pp. 8509-8517, vol. 29, No. 37.

\* cited by examiner (A) LIP-I (349bp) (SEQ ID NO: 1)

| | |
|---|---|
| AGGGCTGCGTCAACACCAAGGGCAGCTACGAGTGTGTGTGCCCACCAGGG | 50 |
| AGGAGGCTGCACTGGAATCGGAAGGACTGTGTGGAGATGAGCGGGTGCCT | 100 |
| GTCTCGGTCCAAGGCCTCTGCCCAGGCCCAGCTGTCCTGTGGCAAGGTGG | 150 |
| GTGGAGTGGAAAACTGCTTCCTGTCCTGCCTGGGCCAGAGTCTCTTCATG | 200 |
| CCGGACTCAGAAACCAGCTACATCCTGAGCTGTGGTGTTCCAGGTCTCCA | 250 |
| GGGCAAGGCACCACCGAAGCGCAATGGCACCAGCTCCAGTGTGGGGCCCG | 300 |
| GCTGCTCAGATGCCCCACCACCCCCATCAGACAGAAGGCCCGCTTCAA | 349 |

(B) LIP-II (484bp) (SEQ ID NO: 2)

| | |
|---|---|
| CGCCTGGACAGAAATGGCTCCCTACACATCTCGCAGACATGGTCAGGGGA | 50 |
| CATTGGCACGTATACCTGCCGGGTACTCTCAGCTGGTGGCAATGACTCTC | 100 |
| GCAACGCCCACCTGCGAGTCAGGCAGCTCCCCATGCTCCTGAGCACCCC | 150 |
| GTGGCAACACTCAGCACCATGGAGAGACGCGCCATCAACCTGACCCGGGC | 200 |
| TAAACCCTTCGACGGCAACAGCCCTCTGATGCGCTACATCTTGGAGATGT | 250 |
| CGGAAAACGATGCTCCCTGGACCATACTTCTGGCCAGCGTGACCCAGAAG | 300 |
| CCACCTCCGTGATGGTCAAGGGACTGGTTCCCGCTCGTTCTTACCAGTTC | 350 |
| CGCCTCTGCGCTGTCAACGATGTGGGCAAAGGGCAATTCAGCAAGGACAC | 400 |
| AGAAAGGGTCTCCCTTCCTGAGGAGCCCCCACCGCCCCTCCACAGAACG | 450 |
| TCATTGCCAGCGGCCGGACCAACCAATCCATCAT | 484 |

FIG. 4

HIP-I (274 bp) (SEQ ID NO: 3)

| | |
|---|---:|
| ACAGTTTCTCCTTCCCCAACTTCAGTTCTTCCCTCATTCTTACCCATCCA | 50 |
| ATTCTACGCCCCTTATTTCTTGCTCACTTGAAAAAACAAAAACACAAACC | 100 |
| AGATACAACCCTTGCAAAGATATGAAAATTGAAACATAAATATTAAAGCA | 150 |
| AATGACCAATGGCAAAGATTGTCAAGATGAGAGAGGAGACATGACAATTG | 200 |
| CTTCTCAGTTCCTTGTGTATAGACAATGCCTTATGACATGTGTTTATCAC | 250 |
| TCCACTGTAACTAAGATTGTGATT | 274 |

FIG. 7 DNA sequences of the cloned amplicon corresponding to HIP-I

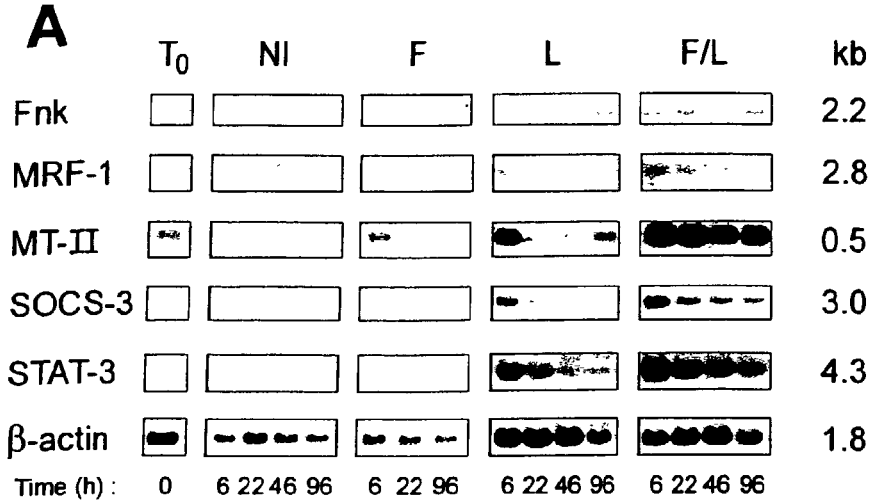
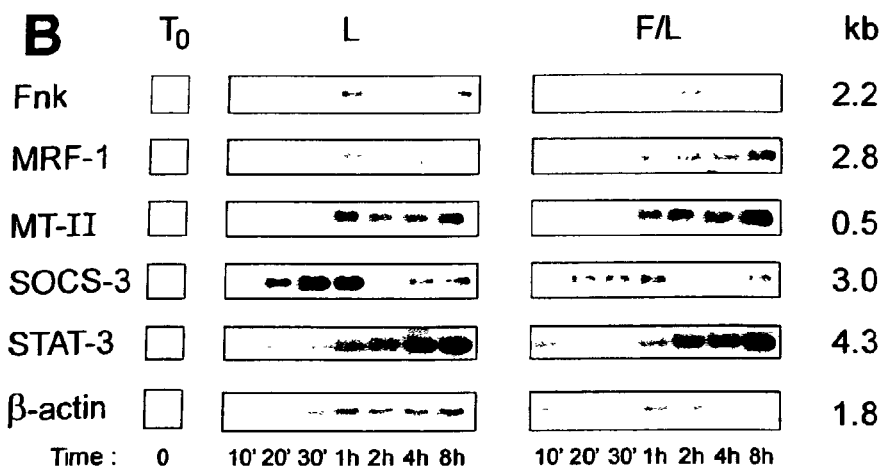
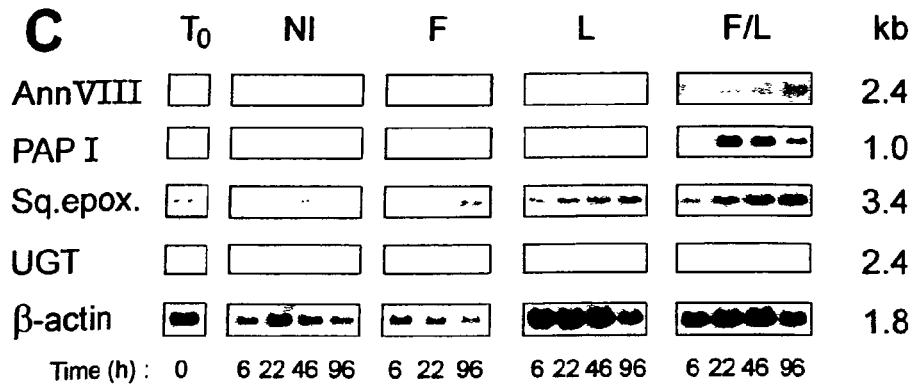
Fig.8

SEQUENCE LISTING

```
<160> NUMBER OF SEQ ID NOS: 11

<210> SEQ ID NO 1
<211> LENGTH: 349
<212> TYPE: DNA
<213> ORGANISM: Artificial Sequence
<220> FEATURE:
<221> NAME/KEY: misc_feature
<223> OTHER INFORMATION: Cloned amplicon from rat LIP-I
      (FIG. 4, portion A)

<400> SEQUENCE: 1
agggctgcgt caacaccaag ggcagctacg agtgtgtgtg cccaccaggg aggaggctgc      60
actggaatcg gaaggactgt gtggagatga gcgggtgcct gtctcggtcc aaggcctctg     120
cccaggccca gctgtcctgt ggcaaggtgg gtggagtgga aaactgcttc ctgtcctgcc     180
tgggccagag tctcttcatg ccggactcag aaaccagcta catcctgagc tgtggtgttc     240
caggtctcca gggcaaggca ccaccgaagc gcaatggcac cagctccagt gtggggcccg     300
gctgctcaga tgcccccacc accccatca gacagaaggc ccgcttcaa                349

<210> SEQ ID NO 2
<211> LENGTH: 484
<212> TYPE: DNA
<213> ORGANISM: Artificial Sequence
<220> FEATURE:
<221> NAME/KEY: misc_feature
<223> OTHER INFORMATION: cloned amplicon from rat LIP-II
      (FIG. 4, portion B)
```

<400> SEQUENCE: 2

```
cgcctggaca gaaatggctc cctacacatc tcgcagacat ggtcagggga cattggcacg        60
tatacctgcc gggtactctc agctggtggc aatgactctc gcaacgccca cctgcgagtc       120
aggcagctcc cccatgctcc tgagcacccc gtggcaacac tcagcaccat ggagagacgc       180
gccatcaacc tgacccgggc taaacccttc gacggcaaca gccctctgat gcgctacatc       240
ttggagatgt cggaaaacga tgctccctgg accatacttc tggccagcgt gacccagaag       300
ccacctccgt gatggtcaag ggactggttc ccgctcgttc ttaccagttc cgcctctgcg       360
ctgtcaacga tgtgggcaaa gggcaattca gcaaggacag agaaagggtc tcccttcctg       420
aggagccccc caccgcccct ccacagaacg tcattgccag cggccggacc aaccaatcca       480
tcat                                                                    484
```

<210> SEQ ID NO 3
<211> LENGTH: 274
<212> TYPE: DNA
<213> ORGANISM: Artificial Sequence
<220> FEATURE:
<221> NAME/KEY: misc_feature
<223> OTHER INFORMATION: cloned amplicon corresponding to HIP-I (FIG. 7)

<400> SEQUENCE: 3

```
acagtttctc cttccccaac ttcagttctt ccctcattct tacccatcca attctacgcc        60
ccttatttct tgctcacttg aaaaaacaaa aacacaaacc agatacaacc cttgcaaaga       120
tatgaaaatt gaaacataaa tattaaagca aatgaccaat ggcaaagatt gtcaagatga       180
gagaggagac atgacaattg cttctcagtt ccttgtgtat agacaatgcc ttatgacatg       240
tgtttatcac tccactgtaa ctaagattgt gatt                                    274
```

<210> SEQ ID NO 4
<211> LENGTH: 24
<212> TYPE: DNA
<213> ORGANISM: Artificial Sequence
<220> FEATURE:
<221> NAME/KEY: misc_feature
<223> OTHER INFORMATION: oligonucleotide adapter molecule R-Bgl-24

<400> SEQUENCE: 4

```
agcactctcc agcctctcac cgca                                               24
```

<210> SEQ ID NO 5
<211> LENGTH: 12
<212> TYPE: DNA
<213> ORGANISM: Artificial Sequence
<220> FEATURE:
<221> NAME/KEY: misc_feature
<223> OTHER INFORMATION: oligonucleotide adapter molecule R-Bgl

<400> SEQUENCE: 5

```
gatctgcggt ga                                                            12
```

<210> SEQ ID NO 6
<211> LENGTH: 24
<212> TYPE: DNA
<213> ORGANISM: Artificial Sequence
<220> FEATURE:
<221> NAME/KEY: misc_feature
<223> OTHER INFORMATION: oligonucleotide adapter molecule J-Bgl -continued

```
<400> SEQUENCE: 6
accgacgtcg actatccatg aaca                                          24

<210> SEQ ID NO 7
<211> LENGTH: 12
<212> TYPE: DNA
<213> ORGANISM: Artificial Sequence
<220> FEATURE:
<221> NAME/KEY: misc_feature
<223> OTHER INFORMATION: oligonucleotide adapter molecule J-Bgl

<400> SEQUENCE: 7
gatctgttca tg                                                       12

<210> SEQ ID NO 8
<211> LENGTH: 24
<212> TYPE: DNA
<213> ORGANISM: Artificial Sequence
<220> FEATURE:
<221> NAME/KEY: misc_feature
<223> OTHER INFORMATION: oligonucleotide adapter molecule N-Bgl-24

<400> SEQUENCE: 8
aggcaactgt gctatccgag ggaa                                          24

<210> SEQ ID NO 9
<211> LENGTH: 12
<212> TYPE: DNA
<213> ORGANISM: Artificial Sequence
<220> FEATURE:
<221> NAME/KEY: misc_feature
<223> OTHER INFORMATION: oligonucleotide adapter molecule N-Bgl

<400> SEQUENCE: 9
gatcttccct cg                                                       12

<210> SEQ ID NO 10
<211> LENGTH: 20
<212> TYPE: DNA
<213> ORGANISM: Artificial Sequence
<220> FEATURE:
<221> NAME/KEY: misc_feature
<223> OTHER INFORMATION: forward primer for the pCDNA3 clones

<400> SEQUENCE: 10
gaacccactg cttaactggc                                               20

<210> SEQ ID NO 11
<211> LENGTH: 20
<212> TYPE: DNA
<213> ORGANISM: Artificial Sequence
<220> FEATURE:
<221> NAME/KEY: misc_feature
<223> OTHER INFORMATION: reverse primer for the pCDNA3 clones

<400> SEQUENCE: 11
gtcgaggctg atcagcgagc                                               20
```

LEPTIN-MEDIATED GENE-INDUCTION

CROSS-REFERENCE TO RELATED APPLICATIONS

This application is a continuation of U.S. patent application Ser. No. 09/770,735, filed on Jan. 26, 2001, which became abandoned on Sep. 26, 2003, which is a continuation of International Application No. PCT/EP99/05489, filed on 27 Jul. 1999, designating the United States of America, (International Publication No. WO 00/007014, published Feb. 10, 2000) the entire contents of each of which are incorporated by this reference.

TECHNICAL FIELD

The current invention relates to leptin and/or a cytokine that binds to a receptor complex comprising gp 130, optionally in combination with a compound acting on adenylate cyclase or one of its downstream targets, to activate a signaling cascade wherein, as a result thereof, immediate early response and/or late target genes are induced in neuro-endocrine cells or in cells of neuro-endocrine origin.

BACKGROUND

In healthy conditions, assimilation, storage and utilization of nutrient energy constitute a highly integrated homeostatic system. Maintaining a relatively constant level of energy stores, and hence body weight, requires the achievement of a balance between food intake and energy expenditure. The "set point" hypothesis proposes coordinated regulation by control centers in the central nervous system. Hypothalamic nuclei are believed to be the sites at which the "set point" is regulated, given their important role in establishing homeostasis through regulation of food intake (hunger versus satiety), body weight, energy expenditure (adaptive thermogenesis) and hormone integration involving substrate interconversion, storage and mobilization as appropriate.

An expanding array of (neuro) peptides and neurotransmitters are being discovered that alter food intake when administered peripherally or directly into the hypothalamus. Mouse models of obesity include five apparently single gene mutations. The most intensively studied mutations occur in the ob and db genes which are intimately involved in the control of body fat deposits. This control involves a signaling pathway including a hormone secreted by adipocytes and acting through specific receptors in areas of the brain that govern ingestive behavior and metabolic activity (Flier, 1997; Flier and Maratos-Flier, 1998; Spiegelman and Flier, 1996).

Cloning of the mouse ob gene and its human homologue led to the identification of the ob gene product (ob protein) now named leptin (Zhang et al., 1994). It is secreted primarily by white adipocyte tissue as a non-glycosylated 146-amino acid polypeptide with a MW of 16 kDa. Consistent with its role as the postulated adipose-derived satiety factor, administration of recombinant leptin to ob/ob mice caused rapid reversal of the obese phenotype (Campfield et al., 1995; Halaas et al., 1995; Pelleymounter et al., 1995) by decreasing food intake and increasing energy expenditure. Furthermore, administration of leptin corrects most, if not all of the metabolic and endocrine defects, including sterility, in the ob/ob mice (Chehab et al., 1996).

Leptin displays no apparent sequence similarity to any other known protein. However, based on structure prediction analysis, leptin is identified as a member of the hematopoietic cytokine receptor family carrying the typical four aa-helical bundle structure. Accordingly, its receptor belongs to the class 1 cytokine receptor superfamily. As a cytokine, leptin has a pleiotropic role including effects on the hemopoietic system, immune defense and inflammation, reproduction and pregnancy, regulation of renal function and acceleration of the onset of puberty in female rodents. In addition to its central hypothalamic action, leptin may also exert effects on extraneural tissues extending its metabolic effects. This extended metabolic effects include, repression of fatty acid and lipid synthesis, triacylglyceride depletion of tissues and increased expression of enzymes of fatty acid metabolism and of the uncoupling protein UCP-2, believed to play an important role in thermogenesis. Recent studies show that leptin also plays a role in hematopoiesis, fatty acid homeostasis in cells, hepatic metabolism and protection against TNF-induced toxicity. Leptin also stimulates the proliferation of $CD4^+$T-cells and has a direct effect on endothelial cells, and cells of the gastro-intestinal tract.

Leptin exerts its effects upon binding to a high affinity receptor, the product of the db gene. This receptor was originally cloned from mouse choroid plexus and may exist in at least six isoforms through alternative splicing (Tartaglia et al.,1995; Lee et al.,1996). So far, most attention has been focused on a ubiquitously expressed splice variant with short cytoplasmic tail (OB—Ra), and on the isoform with a long cytoplasmic domain (OB—Rb), which is predominantly expressed in certain nuclei in the hypothalamus. RT-PCR and Northern blot analysis also showed expression of the latter isoform in peripheral tissues including pancreas, liver, lung, kidney and adrenals, intestine and adipose tissues, as well as in endothelial cells and $CD4^+$helper T-cells.

The detailed structure of the murine leptin receptor gene was recently described. In the db/db mice, a point mutation causing the use of a cryptic splice site leads to the expression of a receptor with a truncated cytoplasmic tail which is likely signaling deficient. The fatty (foreign associate) gene in rats appears to be a functional homologue of the mouse db gene, due to a Gln269Pro substitution in the extracellular domain of the receptor, leading to impaired signaling and obesity. Underscoring the evolutionary conserved role of this pathway, homologous mutations were recently described in humans. Severe early-onset obesity was observed in patients with mutations leading to either impaired leptin (Montague et al., 1997) or leptin receptor (Clement et al., 1998) function.

Based on sequence homology and functional aspects, the leptin receptor is considered a member of the Class I cytokine receptor superfamily, and is most closely related to gp 130, the signaling component of the IL-6R complex, and to the LIF and G-CSF receptors. As such, the leptin receptor contains typical motifs involved in signaling such as a JAK tyrosine kinase binding site and a Box 3 involved in recruitment of STAT-3 upon ligand-induced receptor tyrosine phosphorylation. The long isoform is generally believed to be the signaling competent receptor although divergent signaling capacities have been described for the long and short isoforms which both contain the Box 1 motif. The receptor functions as a (ligand-induced) homodimer, independent of gp 130. Leptin binding leads to the activation of JAK2 and multiple STATs (STAT-1, STAT-3 and STAT-5b), however only STAT-3 activation was observed in hypothalamic centers in vivo. In established hepatoma cell lines stably expressing the OB—R long isoform, the leptin receptor appears to be functionally equivalent to the endogenous IL-6R.

One target for leptin action in the hypothalamus is neuropeptide Y (NPY), a key effector of nutritional homeostasis that stimulates appetite. Leptin induces inhibition of NPY biosynthesis and release. The observation that NPY-deficient mice did not completely reverse the obesity phenotype, although NPY is required for full manifestation of the ob/ob phenotype, makes it likely that other leptin targets must exist. Such alternative target candidates include glucagon-like peptide 1 (GLP-1) produced in the brain stem and causing reduced food intake, the melanin-concentrating hormone also involved in hypothalamic regulation of ingestive behavior, the hypothalamic corticotropin-releasing factor (CRF) inhibiting appetite and stimulating metabolism, and the recently described orexins and cocaine- and amphetamine-regulated transcript (CART), a hypothalamic satiety factor. Effects on the expression of the pro-opio-melanocortin gene by leptin have also been described.

Obese humans, except patients carrying the rare, previously identified, mutations in the genes for leptin or its receptor, generally produce higher levels of circulating leptin, suggesting that obesity is associated with "leptin resistance". Such resistance could conceivably occur at several levels: peripheral leptin dysfunction, dysregulation of the saturable leptin transport through the blood brain barrier, and the expression of, and signaling by, the hypothalamic leptin receptor. Variable mechanisms leading to leptin resistance are suggested by studies in murine models (Halaas et al., 1997).

SUMMARY OF THE INVENTION

Activation of STAT-3 protein, and up-regulation of SOCS-3 gene expression have been shown to occur in hypothalamic nuclei by leptin treatment of ob/ob, but not of db/db mice (Vaisse et al., 1996; Bjorbaek et al., 1998). The PC12 cell line appears to be a physiologically relevant cell line to study leptin-induced gene regulation, since three of the identified genes have been implicated in leptin function or obesity in vivo.

To gain more insight into leptin signaling and function, analysis of leptin-mediated gene induction and signaling in the neuro-endocrine-type PC12 cell line was started. Both immediate early response and late target gene sets were identified. The identification of metallothionein-II (MT-II) as a leptin-induced immediate early response gene is of special interest since it was recently shown that mice with targeted disruption of both MT-I and MT-II genes become obese with elevated plasma leptin levels. So far, no other clear physiological role could be attributed to these proteins.

According to the invention, it is further demonstrated that leptin regulates the expression of MT-II in vivo. In addition, leptin-mediated regulation in vivo of the serine/threonine kinase Fnk and of the Pancreatitis Associated Protein I is shown. Both gene transcripts were identified as leptin-induced in PC12 cells, further underscoring the validity of this in vitro model system. Furthermore, new leptin up-regulated transcripts were identified in PC12 cells differentiated towards a neuronal phenotype, as well as transcripts induced via triggering of the gp 130 signaling component of receptors for the interleukin 6 family of cytokines.

Molecules acting downstream of the leptin receptor and modulating leptin function offer potential use in treatment of human obesity or other metabolic disorders including anorexia.

According to the present invention, leptin and/or a cytokine, binds to a receptor complex comprising gp 130, optionally in combination with a compound acting on adenylate cyclase or acting directly or indirectly on one or more of the downstream targets of adenylate cyclase, can be used to activate a signaling cascade wherein as a result thereof, immediate early response and/or late target genes are induced in neuro-endocrine cells or cells of neuro-endocrine origin. The signaling cascade is preferably activated through a leptin receptor while the neuro-endocrine cells are preferably PC12 cells.

The invention also includes leptin and/or a cytokine that binds to a receptor complex comprising gp 130, optionally in combination with a compound wherein the compound is forskolin. In addition, PC12 cells maybe differentiated to a neuronal state upon treatment with b-NGF (beta-nerve growth factor) and forskolin, prior to activation of the receptor complexes.

The use of leptin according to the invention, optionally in combination with forskolin, provides an induction of immediate early response genes such as STAT-3, SOCS-3, Met-allothionein-II (MET-II), the serine/threonine kinase Fnk and MRF-1. The combination of leptin and forskolin has a pronounced induced effect on late target genes such as Pancreatitis Associated Protein I, Squalene Epoxidase, Uridinediphosphate Glucuronyl Transferase and Annexin VIII.

Two additional transcripts encoding Leptin Induced Protein I (LIP-I) and Leptin Induced Protein II (LIP-II) were also identified. LIP-II is a rat orthologue of the human Down Syndrome Cell Adhesion Molecule (DS-CAM). In both cases, no forskolin co-stimulatory effect was observed. On PC12 cells differentiated to a neural phenotype by combined b-NGF and forskolin treatment, Pancreatitis Associated Protein III, Peripherin and Mx2 protein were further identified as being regulated by leptin. Finally, in a RDA experiment to search for transcripts differentially induced by hyper-IL-6 (H-IL-6), as compared to leptin, in PC12 cells, the Reg gene, another member of the Pancreatitis Associated Protein family, and HIP-1 were identified as selectively up-regulated by H-IL-6.

The current invention also includes a method of screening for molecules in mammalian cells, in particular human cells, using human homologues of the genes isolated according to the current invention, that interfere directly or indirectly with the induction of immediate early response genes and/or late target genes or with the activity of the products of the genes. The genes are inducible by leptin and/or a cytokine which binds to a receptor complex comprising gp 130, optionally in combination with a compound acting on adenylate cyclase or acting directly or indirectly on one or more of its downstream targets.

The current invention further includes molecules obtained by this screening method and a pharmaceutical composition comprising the molecule or molecules.

DESCRIPTION OF THE FIGURES

FIG. 1A. Leptin-induced NPY promoter activity in transiently transfected PC12 cells. PC12 cells were co-transfected with control vector (columns 1 and 2), pMET7-mLRsh (columns 3 and 4) or pMET7-mLRlo (columns 5 and 6) together with the pGL3-rNPYluc reporter. The different subcultures were mock stimulated (growth medium alone) or treated with mouse leptin (100 ng/ml) for 72 hours. Luciferase activity in cell lysates is shown; data represent the mean±standard deviation values of assays performed in triplicate.

FIG. 1B. Forskolin co-stimulation on leptin-induced pGL3-rNPY luciferase activity. PC12 cells were transiently co-transfected with pMET7-mRLlo and the pGL3-rNPYluc reporter. Subcultures were treated with mouse leptin alone (filled squares) or in combination with forskolin at a concentration of 10 μM (filled triangles). After 72 hours, cells were lysed and assayed for luciferase activity. Average values of normalized, relative luciferase activities (x-fold increase) from three independent experiments are shown.

FIGS. 1C and 1D. Analysis of b-NGF and forskolin co-stimulation on leptin-induced POMC luciferase (C) or rPAP luciferase activity (D). PC12-LR8 cells were transiently transfected with pGL3-hPOMCluc or pGL3-rPAPluc reporter and treated after two days with forskolin (F: 10 μM), leptin (L: 100 ng/ml), and rat b-NGF (N: 1 ng/ml) as indicated or were left untreated (NI). 24 hours after treatment, cells were lysed and assayed for luciferase activity. Data show the mean value±standard deviation of assays performed in fivefold.

FIG. 2A. Expression of rPAP I mRNA in PC12 cells, transiently transfected with the long isoform of the mouse leptin receptor. PC12 cells were transfected with pMET7-mLRlo and treated for 48 hours with medium (NI, non-induced), leptin (L), forskolin (F) or forskolin plus leptin (F+L). Total RNA was prepared and subjected to RT-PCR analysis for rPAP I. Amplified PCR fragments were visualized on a 1% agarose gel. b-actin amplification was used as a control.

FIG. 2B. Expression of rPAP I mRNA in PC12-LR8 cells. Cells were treated for 48 hours with medium (NI, non induced) or leptin (L). RT-PCR analyses of rPAP I expression. b-actin amplification was used as a control.

PC12-LR8 cells were treated with leptin (L), forskolin (F), or a combination of both (F/L) for the indicated length of time. Hybridization with the mouse b-actin probe was used as a control. NI stands for non-induced control cells. Sizes of transcripts are shown on the right. Exposure times to Biomax MS films were 5.5 days for LIP-I and LIP-II, and 1 day for the corresponding b-actin blot, all at −80° C.

FIGS. 4A and 4B. DNA Sequences of Cloned Amplicons Corresponding to LIP-I and LIP-II.

FIG. 4A (SEQ ID NO: 1) and FIG. 4B (SEQ ID NO: 2) correspond respectively to the cloned amplicons from rat LIP-I and rat LIP-II.

Figure 5:
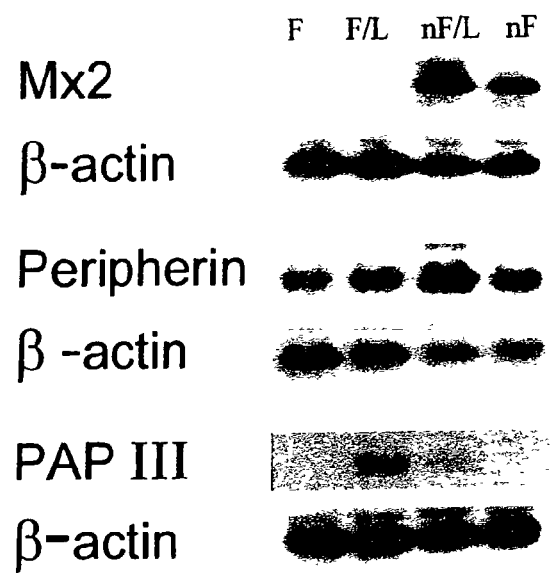

FIG. 5. Northern Blot Analysis of Leptin-Responsive Genes in Differentiated PC12-LR8 Cells and Comparison With the Induction in Non-Differentiated Cells.

Adherent PC12-LR8 cells were treated with b-NGF and forskolin for 5 days to induce neuronal differentiation. Differentiated cells were treated with leptin (nF/L) for 24 hours, or were left untreated (nF), in the continued presence of b-NGF and forskolin. Non-differentiated cells were treated for 24 hours with leptin and forskolin (F/L) or with forskolin alone (F). Hybridization was performed with probes as indicated. Mouse b-actin probe was used as a control. Exposure to BioMax film at −80° C. was 3 days for Mx2, 3 hours for peripherin, 4 days for PAP III and 16 hours for b-actin.

FIGS. 6A and 6B. Comparison of the Induction Patterns of Different Transcripts by Leptin and Hyper-IL-6 in Non-differentiated PC12 Cells Autoradiographs of Northern blot experiments are shown, using mRNA from PC12-LR8 cells treated with either forskolin, leptin, hyper-IL-6, or combinations thereof.

FIG. 6A. Induction patterns of Reg I, HIP-I and peripherin after a 12 hours stimulation with forskolin (F), leptin (L), forskolin plus leptin (F/L), hyper-IL-6 (H) or forskolin plus hyper-IL-6 (F/H). Untreated cells were analyzed as a control (NI). Exposure times to BioMax MS films for Reg I, HIP-I and b-actin were 4 days, 5 days and 3 hours, respectively; and in a separate experiment for peripherin and b-actin, 16 hours and 2 days.

FIG. 6B Induction patterns of PAP I, PAP III, MT-II, Fnk, MRF-1, SOCS-3 and STAT-3 after stimulation with leptin (L) or hyper-IL-6 (H), compared to non-treated control cells (NI). In all cases stimulation was for 12 hours, with the exception of PAP III where stimulation was for 24 hours. b-actin hybridization patterns are shown as control. Exposure times to BioMax MS films at −80° C. were 16 hours for PAP I and 1 hour for b-actin; 4 days for PAP III and 1 hour for b-actin; 3 days for MT-II and Fnk, and 2 days for b-actin; 3 days for MRF-1, 2.5 days for SOCS-3 and 2 days for b-actin; and 16 hours for STAT-3 and 3 hours for b-actin.

FIG. 7. DNA Sequences of the Cloned Amplicon Corresponding to HIP-I (274 bp) (SEQ ID NO: 3).

FIGS. 8A-8C. Kinetics of Induction of Leptin-Responsive Genes in Non-Differentiated PC12-LR8 Cells.

Autoradiographs of Northern blot experiments using PC12-LR8 cells treated as shown and probed for expression of the indicated genes are shown. $T_0$ gives the expression level prior to stimulation. Hybridization with the mouse b-actin probe was used as a control. Sizes of the transcripts are marked on the right.

FIG. 8A. Northern blot analysis of the immediate early response genes. PC12-LR8 cells were left untreated (NI: non induced), or were treated with forskolin (F), leptin (L) or a combination of both (F/L) for the indicated time points. Exposure times to BioMax MS films for the different transcripts were Fnk: 6 days, MT-II: 5 days, MRF-1: 6 days, SOCS-3: 14 hours, STAT-3: 14 hours, b-actin: 5 hours.

FIG. 8B. Immediate early response gene-set: early kinetics. PC12-LR8 cells were treated with leptin alone (L) or with a combination of leptin and forskolin (F/L) for the indicated length of time. Exposure time to BioMax MS films were: Fnk: 3 days, MT-II: 3 days, MRF-1: 3 days, SOCS-3: 2.5 days, STAT-3: 2.5 days, b-actin: 1 hour.

FIG. 8C. Northern blot analysis of the late target genes. PC12-LR8 cells were left untreated (NI), or were treated with forskolin (F), leptin (L) or a combination of both (F/L) for the indicated length of time. Exposure times to BioMax MS films were: Ann VIII: 6 days, PAP I: 14 hours, Squalene Epoxidase: 5 days, UGT: 5 days, b-actin: 14 hours.

Figure 9:
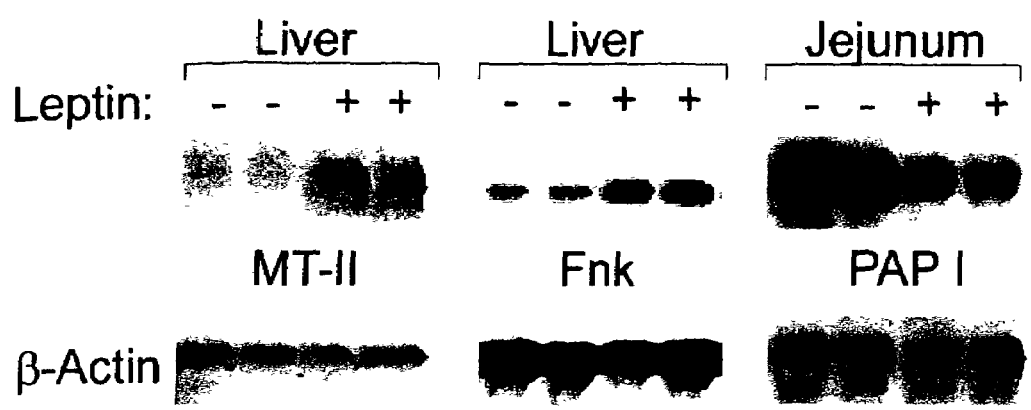

FIG. 9. MT-II, Fnk and PAP I Gene Expression in Leptin Treated ob/ob Mice.

Leptin deficient ob/ob mice were left untreated (−) or were treated with leptin (100 μg; +) intraperitoneally. Mice were killed five hours after treatment. Northern blot analysis of MT-II and Fnk in liver and PAP I expression in jejunum is shown. Hybridization with the mouse b-actin probe was used as a control and is shown below. Exposure times to BioMax MS films were 4 hours, 3 days, 4 hours and 8 hours for MT-II, Fnk, PAP I and b-actin respectively.

FIGS. 10A and 10B. MT-II and Fnk Gene Expression in Starved Wild Type Mice

Wt mice were starved for 36 hours. After 24 hours mice were treated with PBS (−) or leptin (50 μg, supplemented with 200 μg 2A5 anti human leptin antibody;+). At different time points (−24, 0, 2, 6, 12 hours, indicated on top) mice were sacrificed. RNA was extracted from liver tissue (panel A) or jejunum (panel B) and subjected to Northern blot analysis using MT-II and Fnk as probes as indicated. Hybridization with the mouse b-actin probe was used as a control and is shown below. Assays were performed and represented in double. Exposure times to BioMax MS films shown in panel A were 2 hours, 2 days and 3 hours for MT-II, Fnk and b-actin respectively. In panel B exposure times were 2 hours for MT-II and 3 hours for b-actin.

DETAILED DESCRIPTION OF THE INVENTION

As used herein, the term "composition" refers to any composition such as a pharmaceutical composition comprising, as an active ingredient, the molecule or molecules according to the present invention and, to the extent desired, the presence of suitable excipients known to those skilled in the art. The compositions may thus be administered in the form of any suitable composition as detailed below by any suitable method of administration within the knowledge of those skilled in the art.

The preferred route of administration is parenterally. In parenteral administration, the compositions of this invention will be formulated in a unit dosage injectable form such as a solution, suspension or emulsion, in association with a pharmaceutically acceptable excipient. Such excipients are inherently nontoxic and non-therapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives.

The isolated functional molecules of the invention thus obtained are administered at a concentration that is therapeutically effective to prevent allograft rejection, GVHD, allergy and autoimmune diseases. The dosage and mode of administration will depend on the individual. Generally, the compositions are administered so that the isolated functional protein/molecule(s) is given at a dose between 1 mg/kg and 10 mg/kg, more preferably between 10 mg/kg and 5 mg/kg, most preferably between 0.1 and 2 mg/kg. Preferably, it is given as a bolus dose. Continuous short time infusion (during 30 minutes) may also be used. The compositions comprising the isolated functional protein/molecule(s) according to the invention may be infused at a dose between 5 and 20 mg/kg/minute, more preferably between 7 and 15 mg/kg/minute.

The "therapeutically effective amount" of the isolated functional protein according to the invention needed in a specific case, should be determined as being the amount sufficient to cure the patient in need of treatment, or to at least partially arrest the disease and its complications. The amount effective for such use will depend on the severity of the disease and the general state of the patient's health. Single or multiple administrations may be required depending on the dosage and frequency as required and tolerated by the patient.

In the context of this description the terms "molecules", "proteins" and "compounds" are interchangeable unless usage indicates to the contrary.

In order to further disclose the current invention a more detailed explanation is given hereunder.

Synergistic Effects of Leptin and Forskolin or b-NGF on PC12 Cells

In order to study leptin receptor signaling in a neuro-endocrine-related cell type, we transiently transfected PC12 cells with expression vectors for the long or the short isoform of the mouse leptin receptor (pMET7-mLRlo and pMET7-mLRsh respectively) and monitored gene induction by leptin. The PC12 cell line was established from a transplantable rat adrenal pheochromocytoma and is frequently used as a model system for differentiation of neuronal cells. Stimulation with recombinant rat b-nerve growth factor (bb-NGF) leads to a growth arrest and the formation of dendritic processes and expression of neuronal markers. Binding studies using a mouse leptin-SEAP fusion protein, and RT-PCR analysis showed that neither undifferentiated nor differentiated PC12 cells express leptin receptors. To determine leptin responsiveness, different reporter gene constructs were developed, based on the observation that stimulation of the leptin receptor leads to changes in the expression of a variety of neuropeptides, including NPY and POMC. A first reporter construct contains a 500 bp fragment of the rat neuropeptide Y (rNPY) promoter sequence coupled to the luciferase gene (pGL3-rNPYluc).

Figure 1:
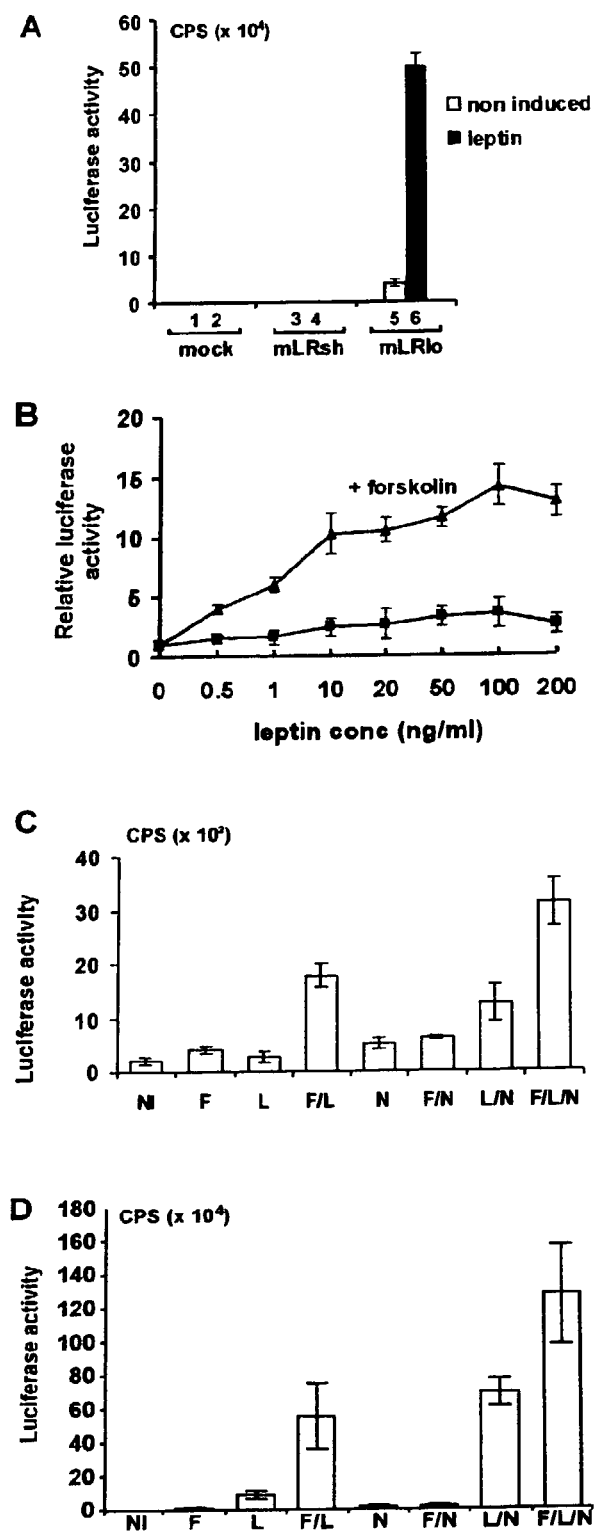
FIGS. 1A-1D. Synergistic Signaling of Leptin and Forskolin in PC12 Cells

FIG. 1, portion A, shows that leptin stimulation of PC12 cells co-transfected with the rNPY reporter construct and pMET7-mLRlo but not with pMET7-LRsh led to a moderate stimulation of luciferase activity. However, co-stimulation in the former case with forskolin, a stimulator of adenylate cyclase, showed an up to 14-fold enhanced reporter activity. Optimal co-stimulatory conditions were determined as 100 ng/ml leptin and 10 µM forskolin (FIG. 1 portion B). This effect was optimal approximately 72 hours post stimulation.

Leptin responsiveness in PC12 cells was further investigated using a clone stably expressing the long isoform of the mouse leptin receptor (PC12-LR8, see below). After transfection of PC12-LR8 with a reporter construct based on the human POMC (proopiomelanocortin) promoter (pGL3-POMCluc) (FIG. 1 portion C), or a reporter construct based on the rat Pancreatitis Associated Protein I promoter (See below) (FIG. 1 portion D), leptin induced luciferase activity was measured. Administration of b-NGF (1 ng/ml) mimicked for both reporter constructs the co-stimulatory action of forskolin. The b-NGF and forskolin effects appeared to be additive in this clone (FIGS. 1 portions C and D).

Identification of Genes Regulated by Leptin in PC12 Cells.

Figure 2:
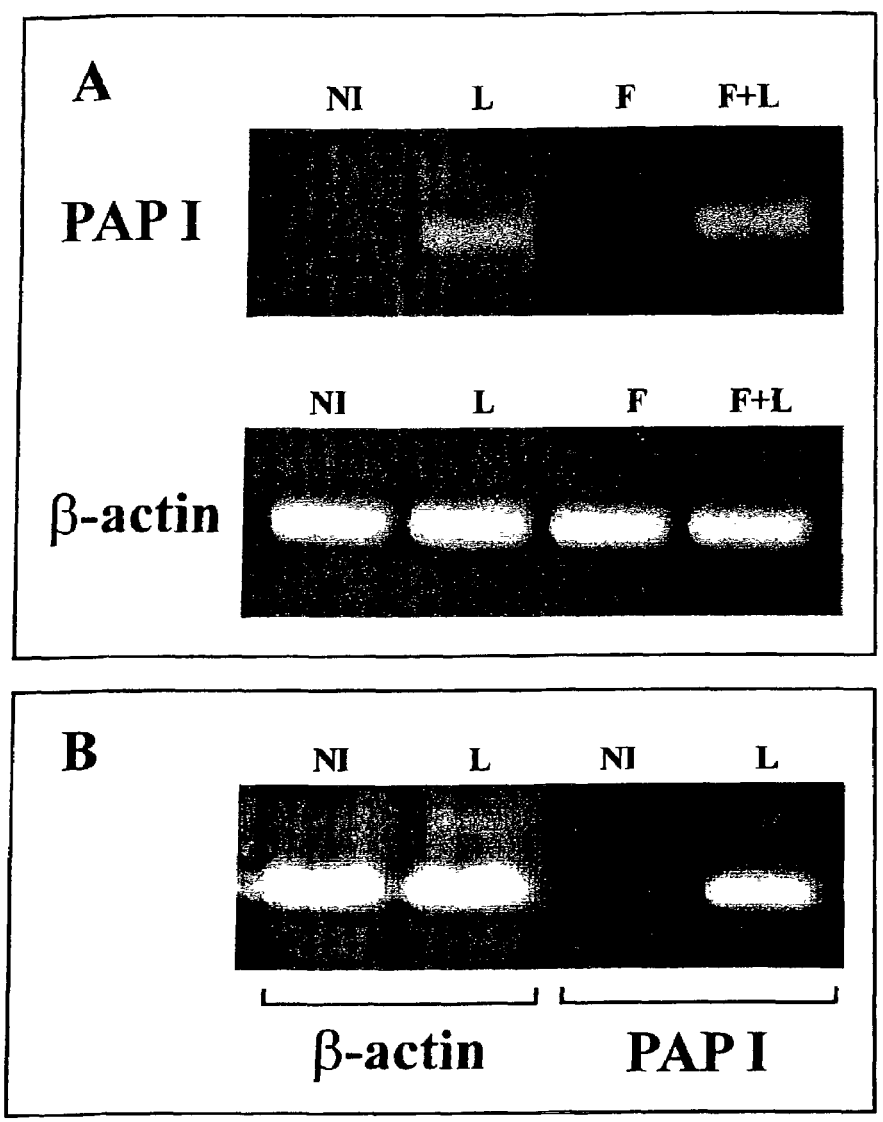
FIGS. 2A and 2B. Selection of a Leptin-responsive PC12 Subclone.

To search for genes regulated by leptin in the PC12 cell line, a RDA (representational difference analysis) experiment was performed using a modification of the original method (Hubank and Schatz, 1994). Using this procedure, it is possible to clone amplicons corresponding to transcripts from leptin-forskolin co-stimulated PC12 cells, transiently transfected with pMET7-mLRlo. After three rounds of subtraction/amplification, selectively amplified bands were purified and subcloned in the pCDNA3 or pCR-Blunt vector (Invitrogen). Subsequent DNA sequencing revealed that a strongly induced transcript encoded the rat Pancreatitis Associated Protein I (rPAP I). Based on this observation, a simple one-tube RT-PCR based procedure was set up to select for PC12 subclones, stably expressing the leptin receptor long isoform (FIG. 2 portion A). One stable clone, PC12-LR8, was chosen for further experiments (FIG. 2 portion B). Individual inserts from the cloned amplicon collection were radiolabeled and leptin-dependent gene regulation was verified and studied in more detail by Northern blot analysis on the PC12-LR8 cell line. A total of 11 leptin-regulated genes were identified, as shown in Table 1. Only up-regulated genes were observed; a parallel experiment selecting for leptin-induced down-modulation of gene expression did not yield any amplicons. Interestingly, several of the identified gene products have already been implicated in leptin signaling or obesity.

Annexin VIII is a calcium-dependent phospholipid-binding protein expressed in lung, skin, liver, and kidney. The physiologic function of annexin VIII remains unknown.

FGF-inducible kinase (Fnk) was first identified as a serine/threonine kinase induced by Fibroblast Growth factor FGF-1 in murine NIH 3T3 fibroblasts. It is closely related to the polo-family of serine/threonine protein kinases (including human Prk, mouse Snk, human and murine Plk, mouse Sak, Drosophila Polo, and yeast Cdc5). In adult animals, Fnk-mRNA is expressed at high levels in skin, but is also detected in brain, intestine, kidney, lung and ovary. In newborn animals, Fnk transcripts are expressed in high levels in intestine, kidney, liver, lung and skin. The related Prk and Plk kinases are induced by cytokines in hematopoietic cells (Li et al., 1996) and in primary T-cells (Holtrich et al., 1994) respectively. These kinases may play a role in cell proliferation, but their precise role remains unclear.

Metallothionein-II (MT-II) is a member of a family of metal-binding proteins that are reported to function in the detoxification and homeostasis of heavy metals, in the scavenging of free radicals and in the acute phase response. Importantly, it was recently reported that MT-I/II deficient mice on a C57BL/6J-12901a genetic background show mild, late onset obesity (Beattie et al., 1998).

Modulator Recognition Factor 1 (MRF-1) is a DNA binding protein belonging to a poorly characterized protein family. (GenBank accession number for sequences of the human homologue and the related human MRF-2 are M62324 and M73837, respectively).

Pancreatitis Associated Protein I (PAP I) is a C-type lectin-related secretory protein present in small amounts in the rat pancreas (in both endocrine and exocrine cells) and is rapidly over expressed during the acute phase of pancreatitis. The physiological role of PAP I is still unclear at present, but its involvement in acute pancreatitis as an acute phase protein suggests a role in tissue protection and/or recovery. PAP I is also expressed in normal intestine and is induced by feeding (Dusetti et al., 1995).

Signal transducer and activator of transcription 3 (STAT-3) is a key transcription factor mediating the signals for a variety of cytokines. A critical role for STAT-3 in leptin signaling has been reported in cell lines (Baumann et al., 1996) and in ob/ob mice (Vaisse et al., 1996).

Squalene epoxidase is a rate-limiting enzyme in cholesterol biosynthesis. Transcriptional regulation of squalene epoxidase by sterol is part of a coordinately controlled biosynthetic pathway (Nakamura et al., 1996).

Suppressor of Cytokine Signaling-3 (SOCS-3) belongs to a growing family of SOCS proteins. These proteins act as intracellular inhibitors of several cytokine signal transduction pathways. It was recently reported that SOCS-3 may contribute to leptin resistance in vivo. (Bjorbaek et al., 1998).

Uridinediphosphate Glucuronyl Transferase (UGT) is a key enzyme involved in bilirubin and drug detoxification, as well as in steroid inactivation and excretion, and in proteoglycan side chain formation. Conjugation of compounds with glucuronic acid renders the molecule strongly acidic and more water soluble at physiological pH than the precursor molecule thereby facilitating metabolism, transport and secretion.

Figure 3:
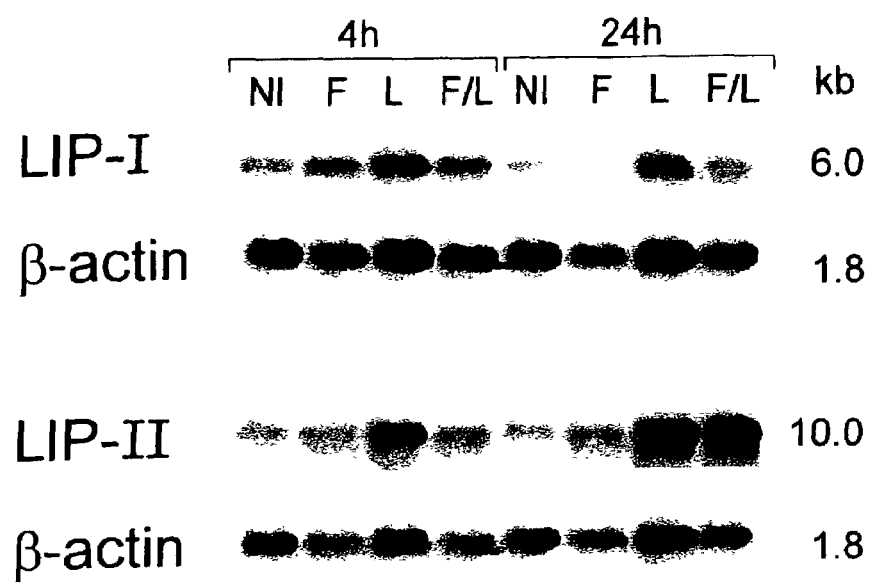
FIG. 3. Northern Blot Analysis of LIP-I and LIP-II Expression in Undifferentiated PC12 Cells.

Two amplicons were cloned respectively derived from transcripts from so far unidentified genes coding for Leptin Induced Proteins LIP-I and LIP-II (FIGS. 3, 4). LIP-II belongs to the immunoglobulin superfamily and is a rat orthologue of the human Down Syndrome Cell Adhesion Molecule, DSCAM. Expression of DSCAM occurs primarily in the brain, and has been implicated in neural development.

These Leptin Induced Proteins LIP-I and LIP-II are hitherto unknown and are therefore new identified nucleic acid/protein sequences as such and thus form part of the current invention.

The search for leptin-regulated genes was also extended to differentiated PC12 cells (FIG. 5). Adherent PC12-LR8 cells were treated with b-NGF and forskolin for 5 days, which led to a growth arrest, the formation of branched neuritic processes and the accumulation of small vesicles. Again, a RDA experiment was performed using mRNAs from differentiated cells treated with leptin for 24 hours, or from untreated cells, both in the continued presence of b-NGF and forskolin. Three leptin up-regulated transcripts were identified (Table 1). Interestingly, one of the gene products, PAP III, belongs to the same protein family as PAP I.

Mx2 is a type I interferon-inducible gene, involved in antiviral defense. High expression levels are observed in differentiated PC12 cells, in contrast to very weak expression in undifferentiated cells.

Peripherin is a cytoskeletal component, which is part of the type III intermediate filament. Increased expression levels are observed in differentiated cells when compared to undifferentiated cells. Up-regulation has been described by Interleukin 6 (IL-6) and Leukemia inhibitory Factor (LIF).

Pancreatitis Associated Protein III (PAP III) is a member of the PAP family of C-type animal lectins, mentioned above. It is also induced in normal intestine upon feeding (Dusetti et al., 1995).

Figure 6:
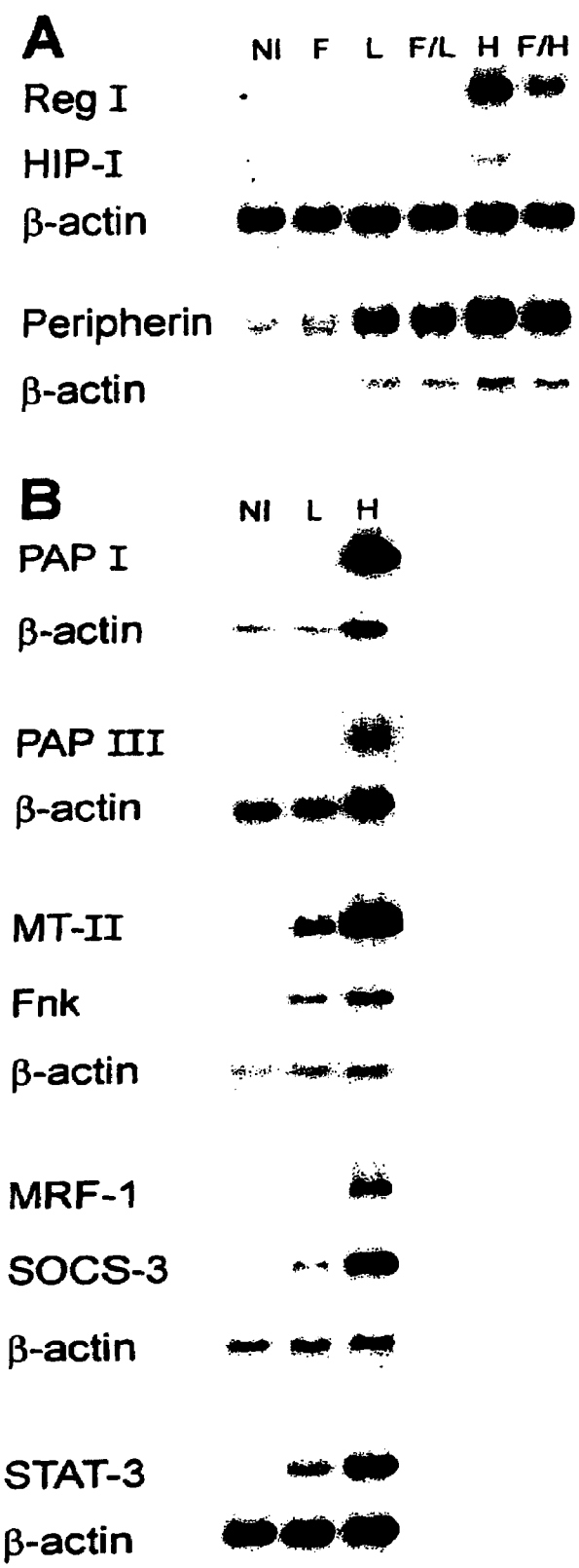

Another RDA experiment was performed to identify transcripts differentially (and selectively) induced by hyper-IL-6 (H-IL-6), as compared to leptin (FIG. 6). H-IL-6 is a fusion protein of IL-6 and the secreted IL-6R subunit (Fischer et al., 1997). In most cases, H-IL-6 treatment led to up-regulation of the same gene-set as observed with leptin. Two H-IL-6 induced transcripts, not induced by leptin, were identified. HIP-I (Hyper-IL-6 induced protein I) corresponds to a novel gene transcript (FIG. 7). Reg is another member of the PAP family of C-type lectins. Reg was originally isolated from a cDNA library from regenerating rat pancreas islets. Other names are Pancreatic Stone Protein (PSP), Pancreatic Thread Protein (PTP), Islet Cell Regenerating Factor and Lithostatin. It is considered as a growth factor for pancreatic beta cells. Similarly, the previously identified, related transcripts encoding PAP I and PAP III, also appear to be strongly induced by H-IL-6, in contrast to leptin, which requires forskolin co-stimulation.

Kinetics of Induction Identifies Immediate Early Response Genes and Late Target Genes.

Next, the kinetics of induction of the above-mentioned transcripts in non-differentiated PC12 cells was analyzed upon leptin treatment. Interestingly, two types of gene-sets could be distinguished: a group of immediate early response genes, including Fnk, MT-II, MRF-1, STAT-3 and SOCS-3, in which case induction occurs within 4 hours (FIG. 8 portion A), and a series of late activated target genes including PAP I, UGT, Ann VIII and squalene epoxidase, with induction not before 6 hours after stimulus (FIG. 8 portion C). Next the induction of the immediate early response genes was investigated in more detail (FIG. 8 portion B). Optimal stimulation varied between 30 minutes (SOCS-3) and 8 hours (STAT-3) post induction. Kinetics of synthesis of SOCS-3 mRNA showed a rapid decline already 2 hours post stimulation. In case of the late target gene-set, optimal mRNA levels were observed between 22 hours (PAP I, UGT) and over 96 hours (Annexin VIII, Squalene epoxidase) post induction.

As is apparent from FIG. 8, the forskolin co-stimulation also allows distinguishing both gene-sets. In case of the immediate early response genes, some co-stimulation is apparent for MT-II and MRF-1 but only at later time points, and not in the early induction phase. In case of SOCS-3, forskolin co-treatment even leads to a reduced induction. In contrast, a strong co-stimulatory effect is seen in case of PAP I, UGT, Ann VIII and squalene epoxidase from 22 hours post stimulation.

To address the mechanism of induction of the late gene set, the effect of the protein synthesis inhibitor cycloheximide on rPAP I and Annexin VIII mRNA expression was measured. Treatment with cycloheximide (50 mmM, starting at 30 minutes before induction for 8.5 hours) showed a strongly reduced expression 24 hours post induction, implying that de novo protein synthesis is required for induction of the late target gene set.

Regulation of MT-II, Fnk and PAP I Expression by Leptin in ob/ob Mice.

In order to assess the value of our in vitro model system for obesity, we investigated the regulation by leptin of a subset of the identified genes in vivo. Recombinant human leptin (R&D Systems) was administered intraperitoneally to leptin deficient ob/ob mice in a single dose of 100 µg leptin /mouse. Mice were killed by cervical dislocation 5 hours after treatment and total RNA was isolated from liver and jejunum. Northern blot analysis was performed using respectively MT-II, Fnk and PAP I as probe (FIG. 9). Leptin treatment of ob/ob mice caused a clear induction of MT-II and Fnk mRNA expression in liver, while expression of PAP I in jejunum was downregulated by leptin. In a separate experiment 3 out of 4 ob/ob mice showed clear induction of MT-II and Fnk mRNA in liver two hours after stimulation with leptin (100 µg/mouse) in combination with the 2A5 antibody (200 µg/mouse). 2A5 has been shown before to potentiate leptin activity in vivo (Verploegen et al., 1997). Twelve hours after injection, expression levels returned to control levels.

Effects of Starvation on MT-II, Fnk and PAP I Expression in Wild Type Mice.

Figure 10:
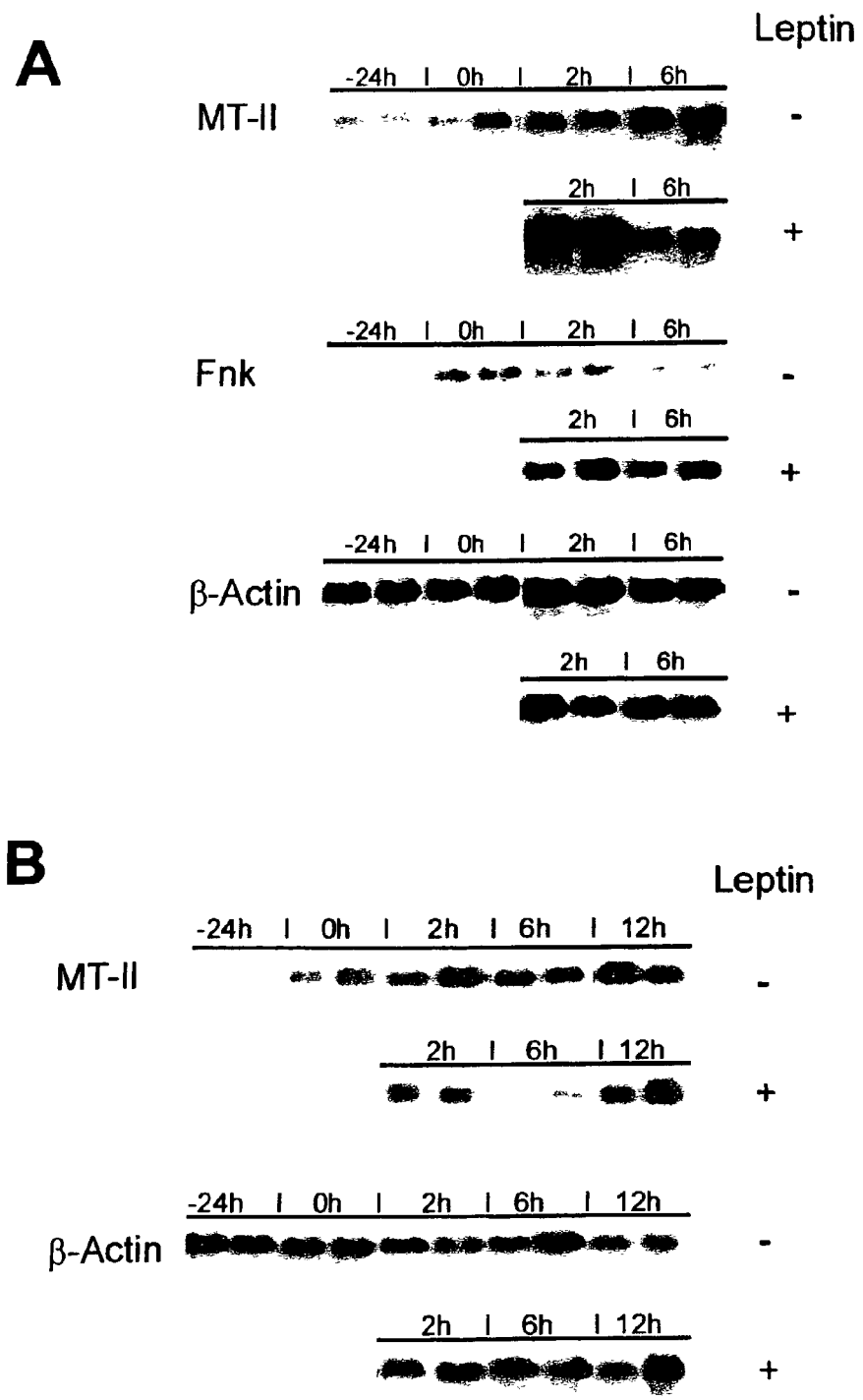

We also investigated the effect of starvation on MT-II and Fnk expression in liver of wild type mice (FIG. 10 portion A). Mice, starved for 24 hours, received a single injection of human leptin intraperitoneally (R&D Systems, 50 µg/mouse) in combination with the 2A5 anti-human leptin antibody (200 µg/mouse). As a control, a single injection with endotoxin free PBS was performed similarly. The leptin effect was evaluated by Northern blot analysis after 2, 6 and 12 hours in prolonged starvation conditions. Starvation conditions led to a moderate increase in MT-II and Fnk mRNA expression in the liver. This effect was markedly enhanced by leptin plus 2A5 treatment, leading to a strong induction of MT-II and Fnk expression two hours post injection. Six hours after leptin administration MT-II mRNA expression returned to the level observed in the PBS treated control mice, whereas Fnk expression was maintained at higher expression level, compared to the control group. Starvation also led to a spontaneous induction of MT-II mRNA in jejunum. In contrast with the observation in liver, this effect was suppressed by leptin +2A5 treatment 6 hours post injection. The expression levels of MT-II recovered to control levels 12 hours post injection (FIG. 10 portion B). A similar pattern was observed for PAP I mRNA expression in jejunum, showing a reduction 24 hours after leptin +2A5 treatment in starved mice, compared to the PBS treated controls.

In order to further explain the invention some examples are given for the sake of clarity.

EXAMPLES

Example I

Cell Culture and Transfection.

PC12 cells were cultured in RPMI 1640 medium with glutamax-I (GibcoBRL) containing 10% heat-inactivated foetal calf serum (iFCS) and gentamycin (50 µg/ml). The cells were treated with medium alone or supplemented with 100 ng/ml of mouse leptin (R&D Systems), with forskolin (Sigma) at a concentration of 10 µM or with a combination both, unless otherwise indicated.

For neuronal differentiation, resuspended PC12 were seeded on rat tail collagen (Collaborative Biomedical Products) coated plates at 2-3 $10^6$ cells/25 $cm^2$ flask in RMPI 1640 medium with glutamax-I containing 10% heat-inactivated horse serum, 5% iFCS and gentamycin. After one day of culturing, the non-adherent cell fraction was removed by refreshing the medium. Differentiation was induced by a combined b-NGF(10 ng/ml, R&D Systems) and forskolin (10 µM) treatment for approximately 5 days. Medium was replaced after 2-3 and 5 days.

The pMet7 vector was used as an expression vector for the long and short isoforms of the mouse leptin receptor (designated pMET7-mLRlo and pMET7-mLRsh, respectively). pMet7 is a modified version of the mammalian pME18S expression vector that utilizes the SRaa promoter as described by Takebe (Takebe et al., 1988). PC12 cells were transfected by electroporation using the Equibio "Easyject one" electroporator. Typically, $10^7$ cells were electroporated in 0.4 cm electrode gap cuvettes with 5 µg vector at 300V and 1500C. Cell surface expression of each protein was measured by specific binding of the leptin-secreted alkaline phosphatase fusion protein (see below).

Cos1 cells were maintained in DMEM supplemented with 10% iFCS (GibcoBRL), and were transfected with pMET7-leptin SEAP (a vector expressing the mouse leptin-secreted alkaline phosphatase fusion protein) using lipofectane (Life Technologies). Medium was replaced after 16 h and conditioned medium (CM) was harvested after 64 h. The estimated concentration of the leptin-SEAP fusion protein was approximately 1 µg/ml.

Example II

Selection of Cell Lines Stably Expressing the Long Isoform of the Leptin Receptor.

PC12 cells were electroporated with the pMET7-mLRlo expression vector together with the pHCMV-MCS vector containing the neomycin resistance marker. Transfected cells were selected for growth in RPMI 1640 medium containing glutamax-I (GibcoBRL) and supplemented with 10% heat-inactivated fetal bovine serum and gentamycin (50 µg/ml). Cells were first grown in selective medium containing 500 µg/ml G418 sulfate (Calbiochem) for seven days and in 750 µg/ml G418 from day eight on. After four weeks of growth, colonies were transferred to 48 well plates in medium containing 750 µg/ml G418. Subclones were selected for leptin responsiveness and PAP I gene activation using a one-tube RT-PCR procedure. In brief, after cell lysis mRNA was hybridized with biotin labeled oligodT and captured to streptavidin-coated tubes. After three times washing, the same tubes were used for the RT-PCR, optimized for detection of PAP I gene induction (mRNA capture and Titan One Tube procedure, Boehringer Mannheim).

Leptin Binding Assay

Cell surface expression of leptin receptors on PC12 cells was measured using a mouse leptin-secreted alkaline phosphatase chimeric protein as described (Baumann et al., 1996; Flanagan and Leder, 1990). Briefly, cells were washed 48 h post transfection (wash buffer: RPMI 1640, 0.1% NaN$_3$, 20 mM Hepes pH 7.0, 0.01% TWEEN 20) and were incubated for 90 min at room temperature with a 1/10 dilution of the Cos1 CM containing the chimeric protein in wash buffer. After 6 successive washing steps, cells were lysed in a buffer containing 1% TX-100, 10 mM Tris. HCl pH7.4 and the lysates were treated at 65° C. for 30 min to inactivate endogenous alkaline phosphatases. Alkaline phosphatase activity was measured using the CSPD substrate (Phospha-Light, Tropix) according to the manufacturers specifications in a TopCount.NXT Chemiluminescence Counter (Packard).

Example III

RDA (Representational Difference Analysis).

RDA was used to clone differentially expressed cDNAs from PC12 cells, transiently transfected with the leptin receptor long isoform, or from neuronal differentiated PC12-LR8 cells, which stably express the leptin receptor long isoform. In both cases, cloning was performed using mRNA from cells either stimulated with leptin+forskolin or with forskolin alone. This RDA procedure was essentially performed as originally described (Hubank and Schatz, 1994) and modified by Braun et al. (Braun et al., 1995). PC12 cells were transfected with the pMET7-LRlo expression vector and stimulated for 72 hours with forskolin alone or with a combination of forskolin and leptin. In case of neuronal differentiated PC12-LR8 cells, mRNA was obtained from cells treated with b-NGF and forskolin as described above for 5 days to induce neuronal differentiation, followed by a 24 h treatment with leptin (100 ng/ml) or without additional treatment. In case of hyper-IL-6 treatment, undifferentiated PC12-LR8 cells were treated with either H-IL-6 (5 ng/ml) or leptin (100 ng/ml) for 24 h, prior to mRNA isolation and RDA analysis.

mRNAs were isolated using the Fast Track method (Invitrogen). A 2 µg sample of mRNA of each cell population was used for RDA analysis. cDNAs were synthesized from the mRNAs and digested with DpnII. Two oligonucleotide adapter molecules, 5' AGCACTCTCCAGCCTCTCAC-CGCA 3' (SEQ ID NO: 4) (R-Bgl-24) and 5' GATCTGCG-GTGA 3(SEQ ID NO: 5)(R-Bgl-12), were ligated to the DpnII-digested cDNA. This mixture was amplified by PCR with R-Bgl-24 oligonucleotides, and the adapters were excised with DpnII. A second pair of adapters, 5' ACCGACGTCGACTATCCATGAACA 3' (SEQ ID NO: 6) (J-Bgl-24) and 5' GATCTGTTCATG 3' (SEQ ID NO: 7) (J-Bgl-12) were ligated to the amplified fragments from the leptin-forskolin stimulated cell population and hybridized with the R-Bgl-24 amplified cDNA fragments from the forskolin stimulated cell population (R-Bgl adapters removed) at a ratio of 1:100 for 24 h. The hybridization mix was used as template for amplification by PCR. A second round of subtraction was performed by removing the J-Bgl adapters from this first round PCR product, ligating a third pair of oligonucleotide adapters, 5' AGGCAACTGTGC-TATCCGAGGGAA 3' (SEQ ID NO: 8) (N-Bgl-24) and 5' GATCTTCCCTCG 3' (SEQ ID NO: 9) (N-Bgl-12), and hybridizing with driver amplicons at a ratio of 1:800. A third round of subtraction and amplification was performed using the same conditions as in the first round. Subsequently the transcripts were subcloned into the pCDNA3 or pCR-Blunt (Invitrogen) vector. Most insert DNAs were sequenced using the Alf Express Sequencer (Pharmacia) with the Autoread Sequencing Kit according to the manufacturer's specifications. Primers for sequencing the inserts were the C15-labeled M13 forward primer for the pCR-Blunt clones, and the 5'-GAACCCACTGCTTAACTGGC (SEQ ID NO: 10) forward and 5'-GTCGAGGCTGATCAGCGAGC (SEQ ID NO: 11) reverse primers for the pCDNA3 clones. In other cases, sequencing was using an ABI Prism 377 DNA sequencer (Perkin Elmer) using the M13 forward primer.

Example IV

Northern Blot and Reporter Analysis.

Total RNA was prepared from PC12 cells using RNe-asy™ method (Qiagen). RNA (10 µg) was separated on a 1.5% agarose,6% formaldehyde gel, transferred to a nylon membrane (Zeta-Probe GT Genomic, Bio-Rad), and cross-linked using UV radiation. The filters were hybridized for one hour at 68° C. in ExpressHyb™ solution (Clontech) with [$^{32}$P]dCTP-labeled DNA-probes and washed 3 times with 2×SSC, 0.05% SDS at room temperature and twice in 0.1×SSC, 0.1% SDS at 50° C. Autoradiographs were obtained by exposing the blots to BioMax MS film (Kodak) with intensifying screens at −70° C. All Northern blots were normalized by hybridization using a b-actin probe.

Luciferase activity was measured in transfected cells by chemiluminescence. Briefly, 1×10$^5$ were lysed in 100 µl of lysis buffer (25 mM Tris, pH 7.8 with H$_3$PO$_4$; 2 mM CDTA; 2 mM DTT; 10% glycerol; 1% Triton X-100). 70 µl of luciferase substrate buffer (20 mM Tricine; 1.07 mM (MgCO$_3$)$_4$Mg(OH)$_2$5H$_2$O; 2.67 mM MgSO$_4$; 0.1 mM EDTA; 33.3 mM DTT; 270 µM Coenzyme A (lithium salt); 470 µM Luciferin (Duchefa); 530 µM ATP, final pH 7.8) was added to 100 µl of cell lysate and measured for 5 seconds by TopCount.NXT Chemiluminescence Counter (Packard).

Example V

Analysis of Gene Expression In Vivo

Specific pathogen-free female C57BL/6J-Lep$^{ob}$ mice, 9 weeks old at the beginning of the experiment further referred to as ob/ob were obtained from The Jackson Laboratory (Maine, USA). Specific pathogen-free C57BL/6NCrlBr mice, 8 weeks old at the beginning of the experiment, further referred to as wildtype (wt) were obtained from Charles Rivers Labs. The animals were housed in a temperature-controlled environment with 12 hour light/dark cycles and received water and food ad libitum, with exception for the starvation experiment. All experiments were performed according to the European Guidelines on Animal Care and Use. Recombinant human leptin (R&D Systems) was diluted in endotoxin free PBS and administered intraperitoneally in a dose of 100 µg/mouse. In case of co-administration of2A5, a monoclonal antibody raised against human leptin (Verploegen et al., 1997), the dose of leptin was reduced to 50 µg/mouse. The dose of the antibody was 200 µg/mouse. The endotoxin content of the antibody was 0.07 ng/mg protein, as assessed by a chromogenic Limulus amebocyte lysate assay (Coatest, Chromogenix, Stockholm, Sweden). Animals were sacrificed using cervical dislocation. Tissues were resected immediately and frozen in liquid nitrogen. RNA extraction and Northern blot analysis was performed as described above.

TABLE 1

Characteristics of the identified amplicons.

| Identity of the target gene | Sizes of the different amplicons (bp) | Number of subcloned amplicons | Length of corresponding transcript (kb) | RDA number |
|---|---|---|---|---|
| Annexin VIII (Ann VIII) | 405 | 2 | 2.0 | 1 |
|  | 327 | 1 |  |  |
| Fibroblast Growth Factor-Inducible Kinase (Fnk) | 364 | 3 | 2.5 | 1 |
| Hyper-IL-6 Induced Protein (HIP-I) | 274 | 1 | 1.5 | 3 |
| Leptin Induced Protein - I (LIP-I) | 349 | 1 | 6 | 1 |
| Leptin Induced Protein - II (LIP-II) | 484 | 1 | 10 | 1 |
| Metallothionein - II (MT-II) | 317 | 5 | 0.7 | 1 |
| Modulator Recognition Factor - 1 (MRF-1) | 358 | 1 | 2.0 | 1 |
| Mx2 protein | 227 | 1 | 2.0 | 2 |
| Pancreatitis Associated Protein - I (PAP I) | 420 | 2 | 1.0 | 1 |
|  | 462 | 1 |  | 1 |
|  | 494 | 2 |  | 1 |
|  | 418 | 3 |  | 3 |
|  | 496 | 3 |  | 3 |
| Pancreatitis Associated Protein - III (PAP III) | 261 | 8 | 0.6 | 2 |
| Peripherin | 300 | 3 | 1.8 | 2 |
| Regenerating protein I (Reg I) | 214 | 3 | 1.2 | 3 |
|  | 219 | 1 |  |  |
|  | 306 | 3 |  |  |
| Signal Transducer and Activator of Transcription - 3 (STAT-3) | 300 | 2 | 4.5 | 1 |
|  | 361 | 2 |  |  |
| Squalene Epoxidase | 322 | 1 | 3.0 | 1 |
| Suppressor of Cytokine Signaling-3 (SOCS-3) | 389 | 1 | 3.0 | 1 |
| Uridinediphosphate Glucuronyl Transferase (UGT) | 361 | 10 | 2.5 | 1 |

Table 1. The lengths of the corresponding transcripts were estimated from northern blot analysis. In the RDA number column 1, 2 and 3 respectively correspond with an RDA experiment from non-differentiated PC12 cells treated with forskolin or forskolin plus leptin; from differentiated PC12 cells maintained in b-NGF and forskolin and treated with leptin or left untreated; or from non-differentiated PC12 cells treated with hyper-IL-6 or leptin, respectively.

REFERENCES

Baumann, H., Morella, K. K., White, D. W., Dembski, M., Bailon, P. S., Kim, H., Lai, C. F., and Tartaglia, L. A. (1996) The fill-length leptin receptor has signaling capabilities of interleukin 6-type cytokine receptors. Proc. Natl. Acad. Sci. U.S.A., 93, 8374-8378.

Beattie, J. H., Wood, A. M., Newman, A. M., Bremner, I., Choo, K. H., Michalska, A. E., Duncan, J. S., and Trayhum, P. (1998) Obesity and hyperleptinemia in metallothionein (-I and -II) null mice. Proc. Natl. Acad. Sci. U.S.A., 95, 358-363.

Bjorbaek, C., Uotani, S., da Silva, S. B., and Flier, J. S. (1997) Divergent signaling capacities of the long and short isoforms of the leptin receptor. J. Biol. Chem., 272, 32686-32695.

Bjorbaek, C., Elmquist, J. K., Frantz, J. D., Shoelson, S. E. and Flier, J. S. (1998) Identification of SOCS-3 as a potential mediator of central leptin resistance. Molecular Cell, 1, 619-625.

Braun, B. S., Frieden, R., Lessnick, S. L., May, W. A., and Denny, C. T. (1995) Identification of target genes for the Ewing's sarcoma EWS/FLI fusion protein by representational difference analysis. Mol. Cell Biol., 15, 4623-4630.

Campfield, L. A., Smith, F. J., Guisez, Y., Devos, R., and Bum, P. (1995) Recombinant mouse OB protein: evidence for a peripheral signal linking adiposity and central neural networks [see comments]. Science, 269, 546-549.

Chehab, F. F., Lim, M. E., and Lu, R. (1996) Correction of the sterility defect in homozygous obese female mice by treatment with the human recombinant leptin. Nat. Genet., 12, 318-320.

Clement, K., Vaisse, C., Lahlou, N., Cabrol, S., Pelloux, V., Cassuto, D., Gourmelen, M., Dina, C., Chambaz, J., Lacorte, J. M., Basdevant, A., Bougneres, P., Lebouc, Y., Froguel, P., and Guy-Grand, B. (1998) A mutation in the human leptin receptor gene causes obesity and pituitary dysfunction. Nature, 392, 398-401.

Dusetti, N. J., Frigerio, J.-M., Szpirer, C., Dagorn, J.-C. and Iovanna, J. L. (1995) Cloning, expression and chromosomal localization of the rat pancreatitis-associated protein III gene. Biochem. J., 307,9-16.

Flanagan, J. G. and Leder, P. (1990) The kit ligand: a cell surface molecule altered in steel mutant fibroblasts. Cell, 63, 185-194.

Fischer, M., Goldschmitt, J., Peschel, C., Brakenhoff, J. P., Kallen, K. J., Wollmer, A., Grotzinger, J., Rose-John, S. (1997) A bioactive designer cytokine for human hematopoietic progenitor cell expansion. Nat. Biotechnol., 15, 142-145.

Flier, J. S. (1997) Leptin expression and action: new experimental paradigms. Proc. Natl. Acad. Sci. U.S.A., 94,4242-4245.

Flier, J. S. and Maratos-Flier, E. (1998) Obesity and the hypothalamus: novel peptides for new pathways. Cell, 92, 437-440.

Halaas, J. L., Boozer, C., Blair, W. J., Fidahusein, N., Denton, D. A., and Friedman, J. M. (1997) Physiological response to long-term peripheral and central leptin infusion in lean and obese mice. *Proc. Natl. Acad. Sci. U.S.A.*, 94, 8878-8883.

Halaas, J. L., Gajiwala, K. S., Maffei, M., Cohen, S. L., Chait, B. T., Rabinowitz, D., Lallone, R. L., Burley, S. K., and Friedman, J. M. (1995) Weight-reducing effects of the plasma protein encoded by the obese gene [see comments]. *Science*, 269, 543-546.

Holtrich, U., Wolf, G., Brauninger, A., Karn, T., Bohme, B., Rubsamen-Waigmann, H., and Strebhardt, K. (1994) Induction and down-regulation of PLK, a human serine/threonine kinase expressed in proliferating cells and tumors. *Proc. Natl. Acad. Sci. U.S.A.*, 91, 1736-1740.

Hubank, M. and Schatz, D. G. (1994) Identifying differences in mRNA expression by representational difference analysis of cDNA. *Nucleic. Acids. Res.*, 22, 5640-5648.

Lee, G. H., Proenca, R., Montez, J. M., Carroll, K. M., Darvishzadeh, J. G., Lee, J. I., and Friedman, J. M. (1996) Abnormal splicing of the leptin receptor in diabetic mice. *Nature*, 379, 632-635.

Li, B., Ouyang, B., Pan, H., Reissmann, P. T., Slamon, D. J., Arceci, R., Lu, L., and Dai, W. (1996) Prk, a cytokine-inducible human protein serine/threonine kinase whose expression appears to be down-regulated in lung carcinomas. *J. Biol. Chem.*, 271, 19402-19408.

Montague, C. T., Farooqi, I. S., Whitehead, J. P., Soos, M. A., Rau, H., Wareham, N. J., Sewter, C. P., Digby, J. E., Mohammed, S. N., Hurst, J. A., Cheetham, C. H., Earley, A. R., Barnett, A. H., Prins, J. B., and O'Rahilly, S. (1997) Congenital leptin deficiency is associated with severe early-onset obesity in humans. *Nature*, 387, 903-908.

Nakamura, Y., Sakakibara, J., Izumi, T., Shibata, A. and Ono, T. (1996) Transcriptional regulation of squalene epoxidase by sterols and inhibitors in HeLa cells. *J. Biol. Chem.*, 271, 8053-8056.

Pelleymounter, M. A., Cullen, M. J., Baker, M. B., Hecht, R., Winters, D., Boone, T., and Collins, F. (1995) Effects of the obese gene product on body weight regulation in ob/ob mice. *Science*, 269, 540-543.

Spiegelman, B. M. and Flier, J. S. (1996) Adipogenesis and obesity: rounding out the big picture. *Cell*, 87, 377-389.

Takebe, Y., Seiki, M., Fujisawa, J., Hoy, P., Yokota, K., Arai, K., Yoshida, M., and Arai, N. (1988) SR alpha promoter: an efficient and versatile mammalian cDNA expression system composed of the simian virus 40 early promoter and the R-U5 segment of human T-cell leukemia virus type 1 long terminal repeat. *Mol. Cell Biol*, 8, 466-472.

Tartaglia, L. A., Dembski, M., Weng, X., Deng, N., Culpepper, J., Devos, R., Richards, G. J., Campfield, L. A., Clark, F. T., Deeds, J., and et, a. (1995) Identification and expression cloning of a leptin receptor, OB-R. *Cell*, 83, 1263-1271.

Vaisse, C., Halaas, J. L., Horvath, C. M., Darnell-JE, J., Stoffel, M., and Friedman, J. M. (1996) Leptin activation of Stat3 in the hypothalamus of wild-type and ob/ob mice but not db/db mice. *Nat. Genet.*, 14, 95-97.

Verploegen, S. A., Plaetinck, G., Devos, R., Van der Heyden, J. and Guisez, Y. (1997) A human leptin mutant induces weight gain in normal mice. FEBS letters, 405, 237-240.

Zhang, Y., Proenca, R., Maffei, M., Barone, M., Leopold, L., and Friedman, J. M. (1994) Positional cloning of the mouse obese gene and its human homologue. *Nature*, 372, 425-432.

---

What is claimed:

1. A method of inducing a target gene, said method comprising:
administering leptin or leptin-receptor agonist, wherein said leptin or agonist binds to a leptin-receptor long-isoform, to a cell to induce said target gene by inducing a Pancreatitis Associated Protein 1 (PAP 1) promoter, inducible through activation of the leptin-receptor long-isoform complex, wherein said target gene is under control of said PAP1 promoter, wherein said cell is a PC12 cell.

2. The method according to claim 1, wherein said target gene is a PAP1 gene.

3. The method according to claim 1, wherein said target gene is located on a reporter construct placed under control of said PAP1 promoter.

4. The method according to claim 1, further comprising administering a compound acting on adenylate cyclase to said cell in combination with said ligand.

5. The method according to claim 4, wherein administering a compound acting on adenylate cyclase comprises administering forskolin.

6. The method according to claim 1, wherein said ligand comprises leptin.

7. The method according to claim 6, further comprising administering forskolin to said PC12 cell in combination with said leptin.

8. A method of inducing a reporter construct, said method comprising:
administering leptin or leptin-receptor agonist, wherein said leptin or agonist binds to a leptin-receptor long-isoform, to a cell to induce a reporter gene by inducing a Pancreatitis Associated Protein 1 (PAP 1) promoter, inducible through activation of the leptin-receptor long-isoform complex, wherein said reporter construct is under control of said PAP 1 promoter.

9. The method according to claim 8, wherein said reporter gene is coupled to a target gene.

10. The method according to claim 9, wherein said target gene is a PAP1 gene.

11. The method according to claim 8, wherein said cell is a PC12 cell.

12. The method according to claim 8, further comprising administering a compound acting on adenylate cyclase to said cell in combination with said ligand.

13. The method according to claim 12, wherein administering a compound acting on adenylate cyclase comprises administering forskolin.

14. The method according to claim 12, wherein said cell is a PC12 cell.

15. The method according to claim 8, wherein said ligand comprises leptin.

16. The method according to claim 15, wherein said cell is a PC12 cell, and further comprising administering forskolin to said PC12 cell in combination with said leptin.

17. A method of inducing a target gene, said method comprising:
administering a ligand, which ligand binds to a leptin-receptor long-isoform, to a PC12 cell to induce said target gene by inducing a Pancreatitis Associated Protein 1 (PAP 1) promoter, inducible through activation of the leptin-receptor long-isoform complex, wherein said target gene is located on a reporter construct placed under control of said PAP 1 promoter.

18. The method according to claim 17, wherein said target gene is a PAP1 gene.

19. The method according to claim 17, further comprising administering a compound acting on adenylate cyclase to said cell in combination with said ligand.

20. The method according to claim 17, wherein said ligand comprises leptin.

* * * * *

UNITED STATES PATENT AND TRADEMARK OFFICE
CERTIFICATE OF CORRECTION

PATENT NO. : 7,291,458 B2
APPLICATION NO. : 10/235264
DATED : November 6, 2007
INVENTOR(S) : Daniel Broekaert et al.

It is certified that error appears in the above-identified patent and that said Letters Patent is hereby corrected as shown below:

On the title page:
In ITEM (56) References Cited,     OTHER PUBLICATIONS
in the Bjorback et al., "Identification…"
reference change "Bjorback" to --Bjorbaek--

In ITEM (56) References Cited,     OTHER PUBLICATIONS, Page 2,
in the Dusetti et al. reference, change
"un-regulated" to --up-regulated--

In the specification:
    COLUMN 4,    LINE 12,     change "maybe" to --may be--
    COLUMN 6,    LINE 18,     change "and2" to --and 2--

Signed and Sealed this

Sixteenth Day of December, 2008

JON W. DUDAS
*Director of the United States Patent and Trademark Office*